(12) United States Patent
Cohen (10) Patent No.: US 9,004,314 B2
(45) Date of Patent: Apr. 14, 2015

(54) GLOVE DISPENSER

(75) Inventor: David Cohen, Union City, CA (US)

(73) Assignee: Belle L. Chou, Union City, CA (US)

( * ) Notice: Subject to any disclaimer, the term of this patent is extended or adjusted under 35 U.S.C. 154(b) by 119 days.

(21) Appl. No.: 13/405,142

(22) Filed: Feb. 24, 2012

(65) Prior Publication Data

US 2012/0298689 A1 Nov. 29, 2012

Related U.S. Application Data

(60) Provisional application No. 61/490,042, filed on May 25, 2011.

(51) Int. Cl.
| | | |
|---|---|---|
| B65H 1/08 | (2006.01) | |
| B65H 1/00 | (2006.01) | |
| A47K 10/24 | (2006.01) | |
| A61B 19/04 | (2006.01) | |

(52) U.S. Cl.
CPC .................................. A61B 19/045 (2013.01)

(58) Field of Classification Search
CPC .... B65D 25/101; B65D 25/102; B65G 59/02; B65H 3/00
USPC ............. 221/46, 63, 197, 36, 34, 35, 52, 254, 221/59, 179, 58, 65; 206/494
See application file for complete search history.

(56) References Cited

U.S. PATENT DOCUMENTS

| | | | | |
|---|---|---|---|---|
| 1,707,578 A | * | 4/1929 | Shaffer | 221/62 |
| 2,509,841 A | * | 5/1950 | Rose | 283/40 |
| 2,634,855 A | * | 4/1953 | Mandel | 221/59 |
| 3,202,316 A | * | 8/1965 | Silver | 221/59 |
| 3,647,114 A | * | 3/1972 | Bleuer | 221/59 |
| 4,616,767 A | * | 10/1986 | Seido | 221/58 |
| 4,789,058 A | * | 12/1988 | Blaney | 206/232 |
| 4,997,105 A | | 3/1991 | Fischer | |
| 5,570,808 A | | 11/1996 | Tassoni | |
| 5,695,065 A | * | 12/1997 | Kennedy et al. | 206/554 |
| 5,765,718 A | | 6/1998 | Grasso et al. | |
| 5,992,683 A | * | 11/1999 | Sigl | 221/59 |
| 6,158,615 A | * | 12/2000 | Hill | 221/154 |
| 6,543,642 B1 | * | 4/2003 | Milliorn | 221/46 |
| 6,997,310 B1 | * | 2/2006 | Fenley | 206/214 |
| 7,063,233 B2 | | 6/2006 | Jordan et al. | |
| 7,273,156 B2 | * | 9/2007 | Gao et al. | 221/47 |
| 7,416,083 B2 | * | 8/2008 | Bando | 206/494 |
| 7,699,189 B2 | * | 4/2010 | Tramontina | 221/36 |
| 7,806,291 B2 | * | 10/2010 | Anderson | 221/33 |
| 2003/0116580 A1 | | 6/2003 | Baughman | |
| 2004/0169047 A1 | * | 9/2004 | Behnke et al. | 221/45 |
| 2006/0273102 A1 | * | 12/2006 | Wieser et al. | 221/59 |
| 2007/0181594 A1 | * | 8/2007 | Thompson | 221/190 |
| 2008/0142536 A1 | * | 6/2008 | Cohen et al. | 221/48 |
| 2009/0191518 A1 | * | 7/2009 | Rappa | 434/129 |
| 2013/0164729 A1 | * | 6/2013 | Rappa | 434/365 |

* cited by examiner

*Primary Examiner* — Rakesh Kumar (74) *Attorney, Agent, or Firm* — QuickPatents; Kevin Prince (57) ABSTRACT

A dispenser is disclosed for flat items such as disposable gloves that are contained within a dispensing bag that has an at least partially-open front side. The dispenser includes a base that has a rear wall and a pair of opposing side walls. A non-opaque cover with a dispensing aperture therethrough is pivotally fixed between each side wall and adapted to swing between an open and a closed position. At least one elastic cord is stretched between each side wall to urge the dispensing bag towards the cover when the cover is in the closed position and the dispensing bag is between the cover and the at least one elastic cord. The front side of the dispensing bag may be non-opaque and open at a dispensing bag aperture therethrough, a temporary adhesive being fixed proximate a periphery of the dispensing bag aperture.

20 Claims, 5 Drawing Sheets

GLOVE DISPENSER

CROSS-REFERENCE TO RELATED APPLICATIONS

This application claims the benefit of U.S. Provisional Patent Application 61/490,042, filed on May 25, 2011, and incorporated herein by reference.

STATEMENT REGARDING FEDERALLY SPONSORED RESEARCH AND DEVELOPMENT

Not Applicable.

FIELD OF THE INVENTION

This invention relates to dispensers, and more particularly to a rubber glove dispenser.

DISCUSSION OF RELATED ART

Prior art disposable glove dispensers are typically adapted to hold the cardboard or pressboard rectangular boxes into which disposable gloves are typically packaged. Such boxes are usually stuffed with the disposable gloves, which results in a user often touching multiple gloves while trying to grasp one of the visible gloves for removal. As medical practitioners' hands are sometimes contaminated, touching multiple gloves while trying to remove one or two gloves from such dispensers can result in the contamination of remaining gloves within the dispenser. Further, such pressboard boxes are opaque, making it difficult to see how many gloves remain in the box. Still further, when only two or three gloves remain in such a box, it can be difficult to reach into the back of the box to remove the gloves.

U.S. Pat. No. 6,543,642 to Milliorn on Apr. 8, 2003, teaches a disposable glove dispenser system that includes a rigid outer container with an opening, the opening aligned with an opening of an inner flexible dispensing bag containing a plurality of gloves. Such a dispenser is limited to the number of gloves that can be contained in the bag since the gloves and bag are not pressed towards the aperture. As such, the last glove must be reachable by inserting one's fingers into the openings. If such a container is too deep, it will be difficult to reach the bottom-most gloves in the bag.

U.S. Pat. No. 5,992,683 to Sigl on Nov. 30, 1999 teaches a clip lift for a sheet dispensing system, wherein an elastic member fixed between two side walls of a container is used to urge a platform towards a dispensing aperture. Sheets or other flat items between the aperture and the platform are urged towards the aperture. Such a platform results in an area between the platform and a bottom wall of the container that is difficult or impossible to access in order to clean. In a medical environment, each area of such a device needs to be accessible for cleaning, and thus such an apparatus is not well-suited for use in a medical environment. U.S. Pat. No. 4,997,105 to Fischer on Mar. 5, 1991 and U.S. 2006/0273102 to Wieser et al. on Dec. 7, 2006 have similar drawbacks.

U.S. Pat. No. 7,063,233 to Jordan et al. on Jun. 20, 2006 teaches a dispenser for gloves and a method of folding the gloves therein. Such a product provides for imparting a bias towards an opening in the dispenser with a springy material, such as resilient foam. However, such a device has the drawback that the last glove in the bundle of gloves necessarily makes contact with the springy material, which may be contaminated after a period of time by virtue of being in a medical environment. Upon subsequent restocking of the dispenser, such contamination may be transferred to the last glove in the bundle of gloves. Further, springy and resilient materials impart a large springy force when compressed, and less of a force as they decompress. As such, the last few gloves in the dispenser are difficult to remove and may even fall inside the dispenser away from the opening. To prevent this, a larger springy material may be used that will continue to impart a force towards the opening in the dispenser even with the last glove in the bundle, but such a larger springy material would impart an even stronger force against the first few gloves in the bundle, making such initial gloves to be removed difficult to remove due to the increased spring force of the larger springy material.

Therefore, there is a need for a glove dispensing system that reduces the chances of contaminating gloves within the dispenser when removing gloves, and that facilitates the removal of gloves by imparting an even bias to the gloves towards a dispensing aperture even when the dispenser is nearing the end of its supply of gloves. Such a needed system would further allow the ready visual inspection of the number of gloves remaining in the dispenser. Such a needed system would be relatively easy to manufacture and use, would lend an aesthetically pleasing look to medical offices and the like, and would be easy to clean. The present invention accomplishes these objectives.

SUMMARY OF THE INVENTION

The present device is a dispenser for flat items such as disposable gloves that are contained within a dispensing bag that has an at least partially-open front side. The dispenser includes a base that has a rear wall and a pair of opposing side walls. A non-opaque cover is pivotally fixed between each side wall and adapted to swing between an open and a closed position. The cover further includes a dispensing aperture therethrough. Further, the cover is pivotally fixed between each side wall with a pivot positioned away from the base and the periphery of each side wall, such that rotation of the cover from the closed position to the open position is possible even with an obstruction positioned immediately adjacent the base.

A biasing means is fixed within the base and is adapted to urge the dispensing bag towards the cover when the cover is in the closed position. The partially-open front side of the dispensing bag is alignable with the aperture in the cover such that the items may be removed through the dispensing aperture and the dispensing bag. In one embodiment, the biasing means is at least one elastic cord stretched between each side wall.

In one embodiment, the front side of the dispensing bag may be non-opaque so that the flat items may be viewed through the cover and the bag. Further, the dispensing bag may be open at a dispensing bag aperture therethrough, the front side of the dispensing bag further including a temporary adhesive fixed proximate a periphery of the dispensing bag aperture. As such, when the front side of the dispensing bag is pressed against an inside surface of the cover, the dispensing bag is temporarily adhered to cover. The dispensing bag may further include an adhesive liner fixable over the temporary adhesive and dispensing bag aperture to seal the dispensing bag aperture until the dispensing bag is positioned within the base.

The present invention is a glove dispensing system that reduces the chances of contaminating gloves within the dispenser when a user removes gloves therefrom. Further, the present system facilitates the removal of gloves even when only a small number of gloves remain in therein. The present invention allows the ready visual inspection of the number of gloves remaining in the dispenser, and provides an aesthetically pleasing look when mounted on a wall or other object, such as in a medical examination room or office. Such a device facilitates the removal of gloves by imparting an even spring bias to the gloves towards the dispensing aperture even when the dispenser is nearing the end of its supply of gloves. Such a device is relatively easy to clean, and may be mounted in various orientations on either a horizontal or vertical surface. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figures 1, 6:
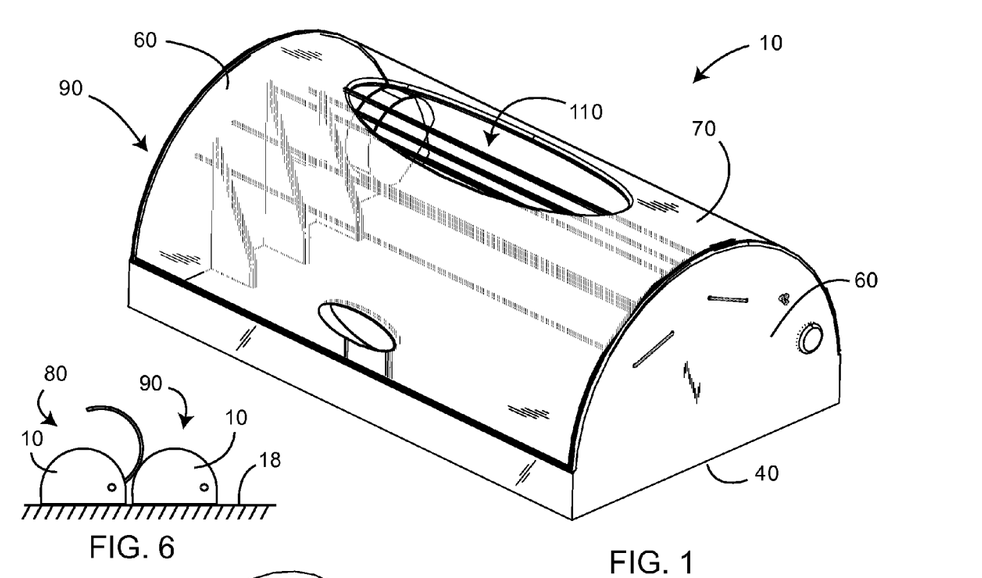
FIG. 1 is a perspective view of a dispenser of the invention, a cover thereof illustrated in a closed position.
FIG. 6 is a top elevational view of two adjacent dispensers, one wherein the cover thereof is in an open position and one wherein the cover thereof is in the closed position.
Figure 2:
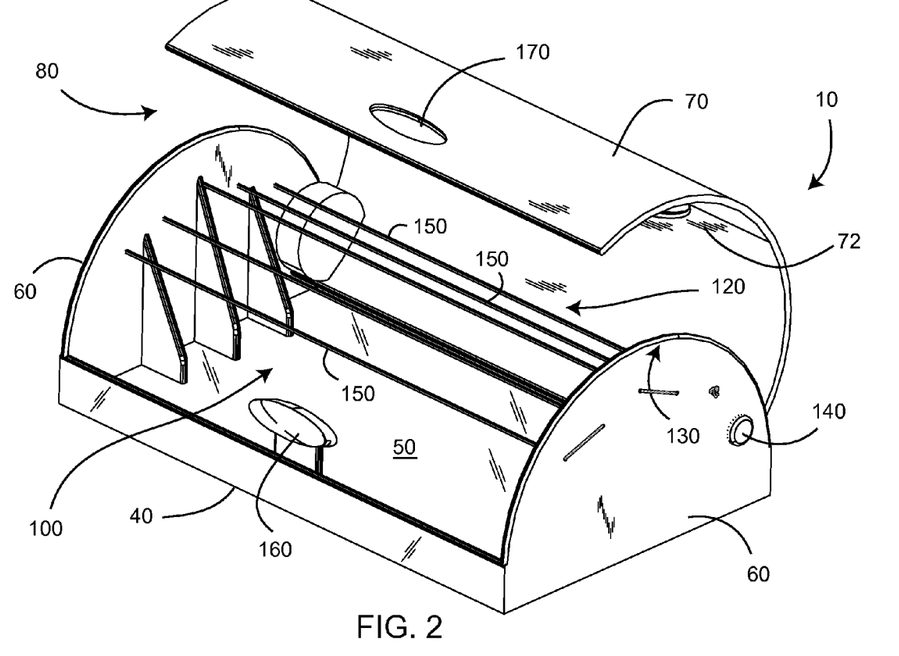
FIG. 2 is a perspective view thereof, illustrated in a partially open position.
Figure 5:
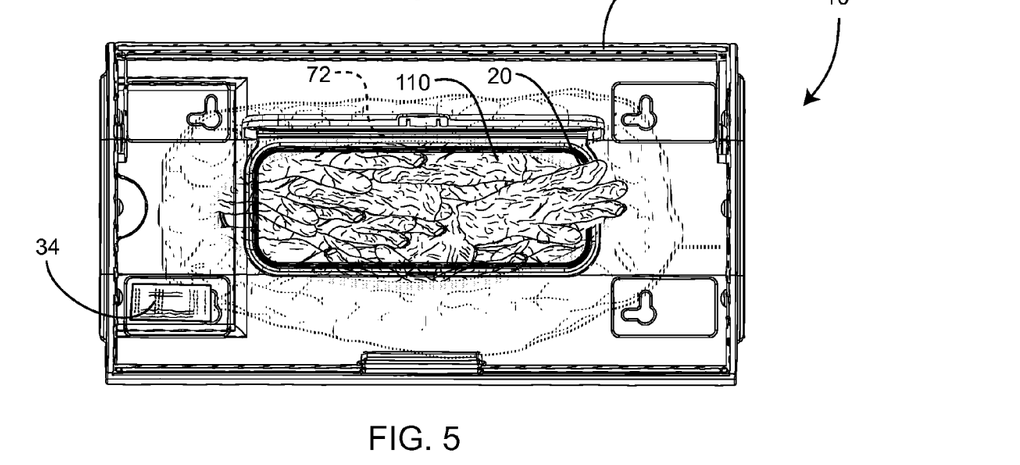
FIG. 5 is a top plan view of the dispensing bag as installed in an alternate embodiment of the dispenser.
Figure 9:
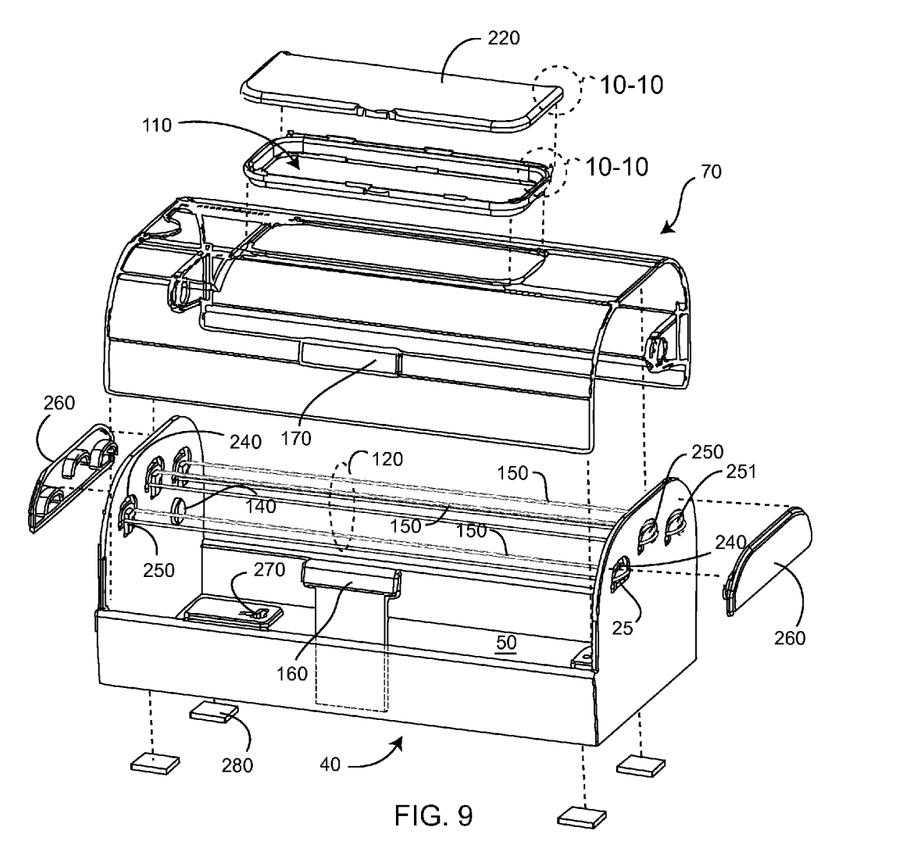
FIG. 9 is an exploded perspective view of the dispenser of FIG. 5.

FIGS. 1, 2 and 5 illustrate a dispenser 10 for flat items 20 that are contained within a dispensing bag 30 that has an at least partially-open front side 32. Such flat items 20 may be silicon or other rubber-based disposable gloves, for example. The dispenser 10 includes a rigid base 40 that has a rear wall 50 and a pair of opposing side walls 60. Each side wall 60 may be in the shape of a half-circle, for example (FIGS. 1 and 2), or truncated rounded rectangles (FIGS. 7 and 9), or other suitable shapes not shown. The base 40 may be made from an injection molded plastic material, a formed metal sheet material, or the like. Preferably the base 40 is made from a material that is relatively easy to clean.

The base 40 may include apertures in the rear wall 50 for mounting to a wall 15 or other structure with a mechanical fastener (not shown) such as headed screws or nails. Such apertures may be L-shaped apertures 270 (FIG. 12), for example, whereby the dispenser 10 may be suspended on the vertical surface in either a portrait or landscape orientation by a plurality of the mechanical fasteners. Alternately, the base 40 may be fixed to the wall 18 or other structure with two-sided adhesive tape (not shown), or the like. The dispenser 10 may further include a plurality of adhesive cushions 280 each adapted to adhere around and cover one of the screw apertures 270 of the rear wall 50 to cushion the dispenser 10 on a horizontal support surface (not shown), or to be applied adjacent to each screw aperture 270 for cushioning the dispenser 10 against the vertical surface 15.

Figure 12:
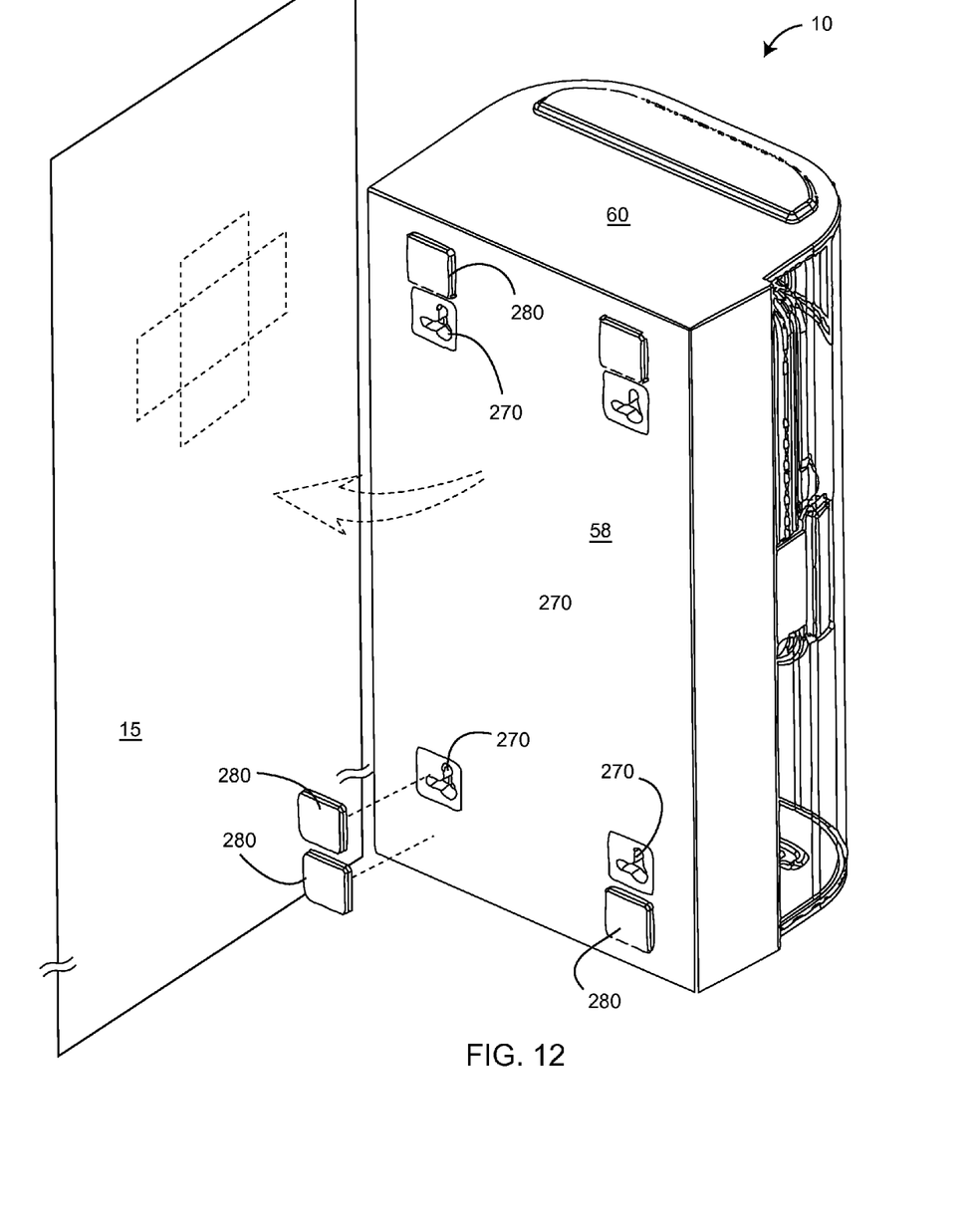
FIG. 12 is a bottom perspective view of the dispenser, showing both horizontal and vertical placement locations on a vertical surface.

Such adhesive cushions 280 when covering each screw aperture 270 further inhibit contamination of the internal space 100.

A rigid non-opaque cover 70 is pivotally fixed between each side wall 60 and adapted to swing between an open position 80 (FIG. 2) and a closed position 90 (FIG. 1). The closed position 90 of the cover 70 is cooperative with the base 40 to define an internal space 100 therebetween. The cover 70 further includes a dispensing aperture 110 therethrough (FIG. 5). The cover 70 may be made from an injection molding process or by heat treating a transparent or translucent sheet of plastic material, for example. The cover 70 is transparent or translucent such that printing or other indicia (not shown) on the disposable bag 30 may be visible therethrough.

Figures 7, 8:
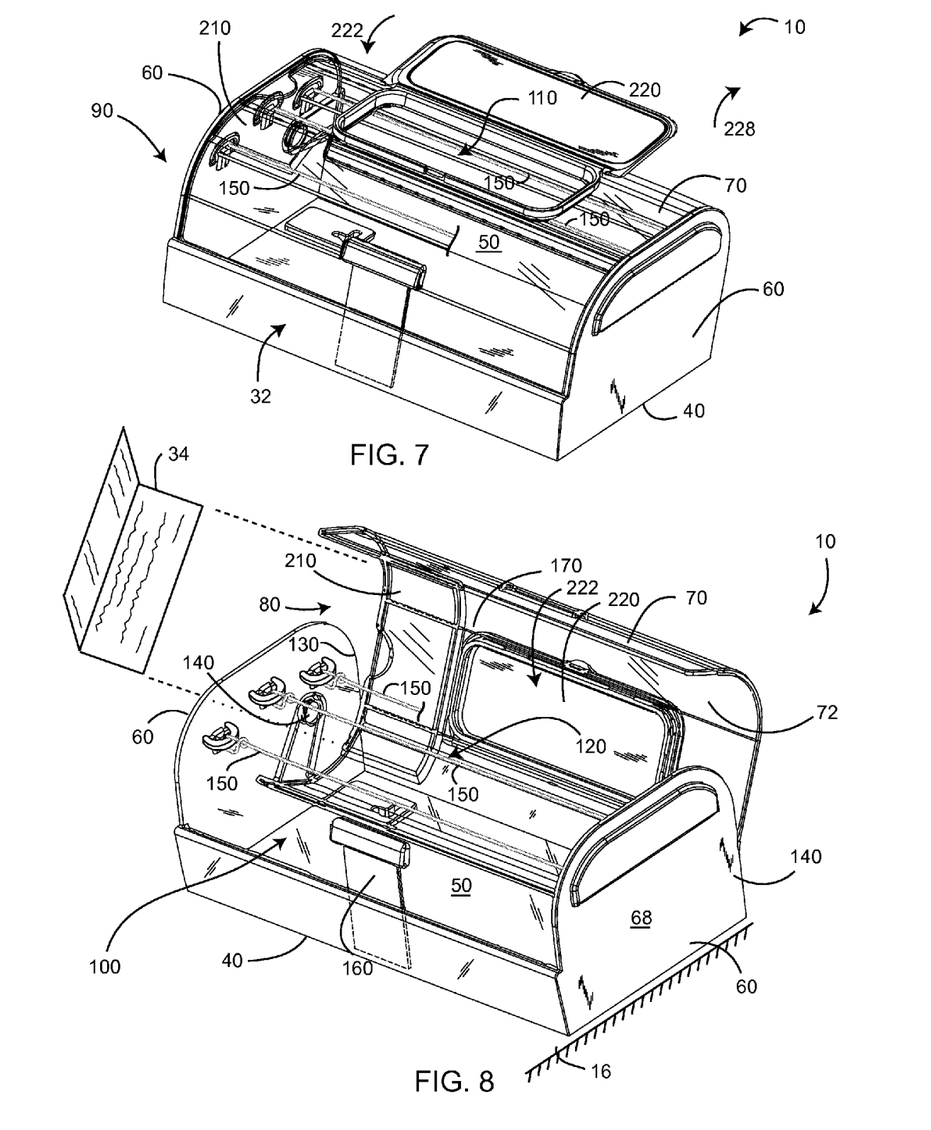
FIG. 7 is a perspective view of the dispenser of FIG. 5, an aperture cover of the cover in an open position.
FIG. 8 is a perspective view of the dispenser of FIG. 5, illustrated with the cover thereof in the partially open position and an information tag exploded away from a tag pocket of the cover.
Figure 11:
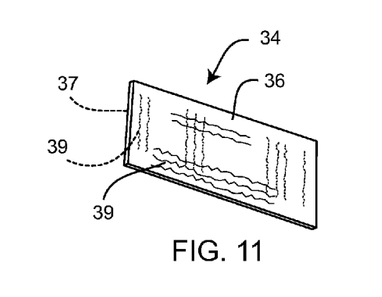
FIG. 11 is a perspective view of a two-sided embodiment of the information tag.

In one embodiment, the cover 70 includes an at least partially non-opaque tag pocket 210 (FIG. 8), such that an information tag 34 (FIGS. 8 and 11) with information regarding the items 20 may be inserted into the tag pocket 210 and read when the cover 70 is in the closed position 90. Such an information tag 34 may be included with the dispensing bag 30, for example, or printed separately. Such an information tag 34 may be two-sided, such that information 39 (FIG. 11) printed on a first side 36 of the information tag 34 is oriented in a landscape orientation, while the same information 39 on an opposing side 37 of the information tag 34 is applied in a portrait orientation. Alternately, the information tag 34 may include the information printed in both landscape and portrait orientations on the first side 36 of the information tag 34, the tag 34 being foldable so that the landscape and portrait orientations are on opposing sides of the folded information tag 34 (FIG. 8).

The cover 70 is arched to conform to the shape of a periphery 130 of the side walls 60. Further, the cover 70 is pivotally fixed between each side wall 60 with a pivot 140 positioned away from the rear wall 50 and the periphery 130 of each side wall 60, such that rotation of the cover 70 from the closed position 90 to the open position 80 is possible even with an obstruction, such as a wall (not shown) or additional dispenser 10 (FIG. 6), positioned immediately adjacent the base 40. The pivot 140 may be a prong that extends through an aperture in each side wall 60, for example, or any other suitable pivoting or hinging arrangement. The pivot 140 may be substantially contained within the internal space 100 such that the side walls 60 are substantially flat on an outer surface 68 thereof. In one embodiment, each base includes an interlock (not shown) such that adjacent dispensers 10 may be mutually fixed together.

A biasing means 120 is fixed within the base 40 and is adapted to urge the dispensing bag 30 towards the cover 70 when the cover 70 is in the closed position 90. The partially-open front side 32 of the dispensing bag 30 is alignable with the aperture 110 in the cover 70 such that the items 20 may be removed through the dispensing aperture 110 and the dispensing bag 30 (FIG. 5).

In one embodiment, the biasing means 120 is at least one elastic cord 150 stretched between each side wall 60. In such an embodiment, the at least one elastic cord 150 traverse a plurality of cord apertures 240 through each side wall 60. Each aperture 240 may include a tab 250 around which at least one elastic cord 150 may be retained. The dispenser 10 may further include a cord cover 260 for each side wall 60 adapted for selective engagement with and covering the plurality of cord apertures 240.

Alternately, the biasing means 120 may be a coil spring (not shown) or a flat spring (not shown) fixed with the rear wall 50. The biasing means 120 may also be a block of resilient foam (not shown) fixed with the rear wall 50, or any equivalent structure or apparatus that biases the dispenser bag 30 towards the aperture 110 of the cover 70.

In one embodiment, the base 40 further includes a resilient latch 160 projecting forward therefrom, the latch 160 adapted to engage a latching aperture 170 formed through the cover 70. As such, when the cover 70 is in the closed position 90, the latch 160 engages the latching aperture 170 of the cover 70 to lock the cover 70 in the closed position 90, pressure applied by the biasing means 120 to the cover thereby prevented from moving the cover 70 away from the closed position 90. The latch 160 may be tapered at a top end thereof (not shown) so that it does not have to be depressed in order to close the cover 70.

Figure 10:
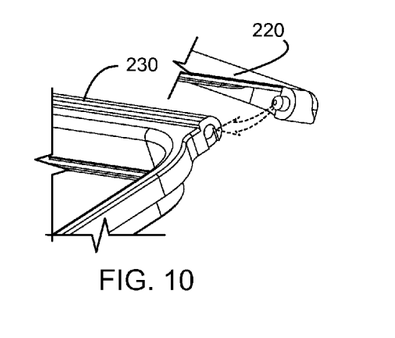
FIG. 10 is an enlarged exploded perspective view of the aperture cover, taken generally along lines 10-10 of FIG. 9.

In one embodiment, the cover 70 includes an apertures cover 220 (FIGS. 7, 9, and 10) that is pivotally fixed to the cover 70 and is adapted to swing substantially 180 degrees between a closed position 222 sealing the dispensing aperture 110 of the cover 70, and an open position 228 that includes a detent 230 adapted to allow selective retaining of the aperture cover 220 in the open position 228.

Figure 3:
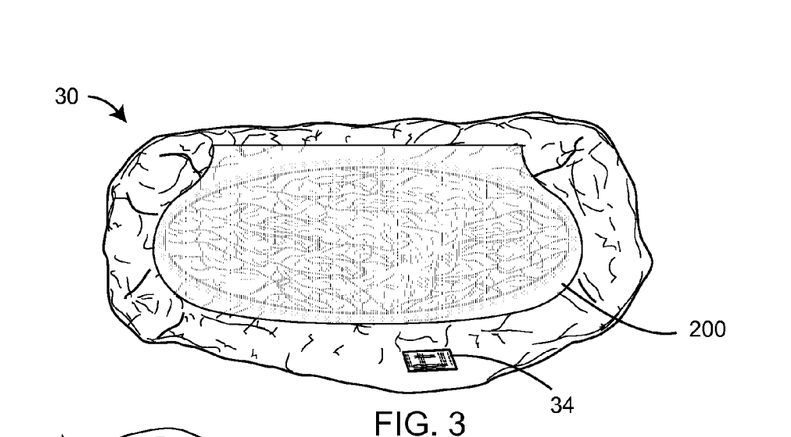
FIG. 3 is a perspective view of a dispensing bag of one embodiment of the invention.
Figure 4:
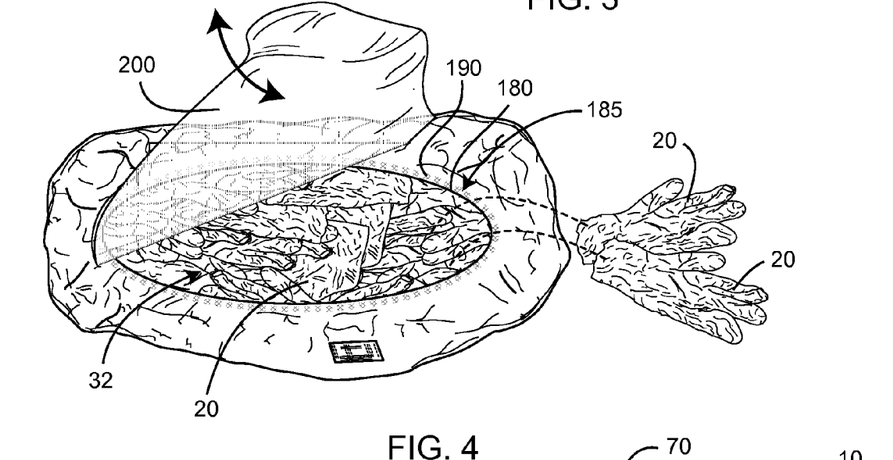
FIG. 4 is a perspective view of the dispensing bag, showing a adhesive liner thereof.

In one embodiment, the dispenser 10 includes the removable dispensing bag 30 with the plurality of flat items 20 therein. In such an embodiment, the front side 32 of the dispensing bag 30 may be non-opaque so that the flat items 20 may be viewed through the cover 70 and the bag 30. Further, the dispensing bag 30 may be open at a dispensing bag aperture 180 therethrough (FIGS. 3-5), the front side 32 of the dispensing bag further including a temporary adhesive 190 fixed proximate a periphery 185 of the dispensing bag aperture 180. As such, when the front side 32 of the dispensing bag 30 is pressed against an inside surface 72 of the cover 70, the dispensing bag 30 is temporarily adhered to cover 70. The dispensing bag 30 may further include an adhesive liner 200 fixable over the temporary adhesive 190 and dispensing bag aperture 180 to seal the dispensing bag aperture 180 until the dispensing bag 30 is positioned within the base 40.

While a particular form of the invention has been illustrated and described, it will be apparent that various modifications can be made without departing from the spirit and scope of the invention. For example, a dispenser 10 having a generally half-cylinder shape has been illustrated in the drawings, however, any other suitable shape, such as box-shaped, triangular shaped, or the like may be used. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A dispenser for flat items contained within a dispensing bag having an at least partially-open front side, comprising:
a rigid base having a rear wall and a pair of opposing side walls;
a rigid non-opaque cover pivotally fixed between each side wall and adapted to swing between an open position and a closed position, the closed position of the cover cooperative with the base to define an internal space therewithin, the cover include a dispensing aperture therethrough;

at least one elastic cord traversing a plurality of cord apertures through each side wall as a biasing means adapted to urge the dispensing bag towards the cover when the cover is in the closed position, the partially-open front side of the dispensing bag alignable with the aperture in the cover such that the items may be removed through the dispensing aperture and the dispensing bag, each aperture including a tab around which at least the one elastic cord may be retained.

2. The dispenser of claim 1 wherein the cover includes an at least partially non-opaque tag pocket, whereby an information tag regarding the items may be inserted into the tag pocket and read.

3. The dispenser of claim 1 wherein the cover includes an aperture cover pivotally fixed to the cover and adapted to swing substantially 180 degrees between a closed position sealing the aperture of the cover, and an open position that includes a detent adapted to allow selective retaining of the aperture cover in the open position.

4. The dispenser of claim 1 wherein the cover is pivotally fixed between each side wall with a pivot positioned away from the rear wall and a periphery of each side wall, whereby rotation of the cover from the closed to the open position is possible even with an obstruction positioned immediately adjacent the base.

5. The dispenser of claim 4 wherein the pivot is substantially contained within the internal space, such that the side walls are substantially flat on an outer surface thereof.

6. The dispenser of claim 1 wherein the base further includes a resilient latch projecting forward therefrom, the latch adapted to engage a latching aperture through the cover, whereby when the cover is in the closed position, the latch engages the latching aperture of the cover to lock the cover in the closed position, pressure applied by the biasing means to the cover thereby prevented from moving the cover away from the closed position.

7. The dispenser of claim 1 wherein the dispenser further includes a cord cover for each side wall adapted for selective engagement with and covering of the plurality of cord apertures.

8. The dispenser of claim 1 wherein the rear wall includes a plurality of L-shaped screw apertures, whereby the dispenser may be suspended on a vertical surface in either a portrait or landscape orientation by a plurality of mechanical fasteners, the dispenser supported by the mechanical fasteners, the mechanical fasteners traversing the vertical surface.

9. The dispenser of claim 8 further including a plurality of adhesive cushions each adapted to adhere around and cover one of the screw apertures of the rear wall to cushion the dispenser on a horizontal support surface, or to be applied adjacent to each screw aperture for cushioning the dispenser against the vertical surface.

10. A dispensing system for flat items, comprising:
a dispensing bag having an at least partially-open front side and adapted for containing the items;
a rigid base having a rear wall and a pair of opposing side walls;
a rigid non-opaque cover pivotally fixed between each side wall and adapted to swing between an open position and a closed position, the closed position of the cover cooperative with the base to define an internal space therewithin, the cover include a dispensing aperture therethrough;
at least one elastic cord traversing a plurality of cord apertures through each side wall as a biasing means adapted to urge the dispensing bag towards the cover when the cover is in the closed position, the partially-open front side of the dispensing bag aligned with the aperture in the cover such that the items may be removed through the dispensing aperture and the dispensing bag, each aperture including a tab around which at least the one elastic cord may be retained.

11. The dispensing system of claim 10 wherein the dispensing bag further includes an adhesive liner fixable over the temporary adhesive and dispensing bag aperture to seal the dispensing bag aperture until the dispensing bag is positioned within the base.

12. The dispenser of claim 10 wherein the cover includes an at least partially non-opaque tag pocket, and wherein the dispensing bag further includes a detachable information tag that is adapted for insertion into the tag pocket, information printed on a first side of the information tag being oriented in landscape orientation and printed on an opposing second side of the information tag in portrait orientation.

13. The dispenser of claim 10 wherein the cover includes an aperture cover pivotally fixed to the cover and adapted to swing substantially 180 degrees between a closed position sealing the aperture of the cover, and an open position that includes a detent adapted to allow selective retaining of the aperture cover in the open position.

14. The dispenser of claim 10 wherein the cover is pivotally fixed between each side wall with a pivot positioned away from the rear wall and a periphery of each side wall, whereby rotation of the cover from the closed to the open position is possible even with an obstruction positioned immediately adjacent the base.

15. The dispenser of claim 14 wherein the pivot is substantially contained within the internal space, such that the side walls are substantially flat on an outer surface thereof.

16. The dispensing system of claim 10 wherein the front side of the dispensing bag is open at a dispensing bag aperture therethrough, the front side of the dispensing bag further including a temporary adhesive fixed proximate the periphery of the dispensing bag aperture, whereby when the front side of the dispensing bag is pressed against an inside surface of the cover the dispensing bag is temporarily adhered thereto.

17. The dispenser of claim 10 wherein the dispenser further includes a cord cover for each side wall adapted for selective engagement with and covering of the plurality of cord apertures.

18. The dispenser of claim 10 wherein an outside surface of the rear wall includes a plurality of L-shaped screw apertures, whereby the dispenser may be suspended on a vertical surface by a plurality of screws traversing the screw apertures, the dispenser supported by the screws, the screws traversing the vertical surface.

19. The dispenser of claim 18 further including a plurality of adhesive cushions each adapted to adhere around and cover one of the screw apertures of the rear wall to cushion the dispenser on a horizontal support surface, or to be applied adjacent to each screw aperture for cushioning the dispenser against the vertical surface.

20. The dispenser of claim 10 wherein the base further includes a resilient latch projecting forward therefrom, the latch adapted to engage a latching aperture through the cover, whereby when the cover is in the closed position, the latch engages the latching aperture of the cover to lock the cover in the closed position, pressure applied by the biasing means to the cover thereby prevented from moving the cover away from the closed position.

\* \* \* \* \*